US006544467B2

(12) United States Patent
Symons et al.

(10) Patent No.: US 6,544,467 B2
(45) Date of Patent: Apr. 8, 2003

(54) EXHAUST GAS SENSOR AND THE METHOD OF MANUFACTURE THEREOF

(75) Inventors: Walter T. Symons, Grand Blanc, MI (US); Kaius K. Polikarpus, Grand Blanc, MI (US); Kerry J. Gross, New Lothrop, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/740,166

(22) Filed: Dec. 18, 2000

(65) Prior Publication Data

US 2002/0113343 A1 Aug. 22, 2002

(51) Int. Cl.[7] ........................................ C04B 33/32

(52) U.S. Cl. ...................... 264/618; 264/624; 264/650; 264/669; 264/670; 264/166; 156/89.12; 156/89.16

(58) Field of Search ................................ 264/618, 650, 264/166, 624, 669, 670; 156/89.12, 89.16

(56) References Cited

U.S. PATENT DOCUMENTS 3,780,150 A * 12/1973 Stetson ...................... 264/650
4,056,588 A 11/1977 Baniel et al.
4,399,090 A * 8/1983 Sprangers .................. 264/650
4,966,742 A * 10/1990 Khouvy ...................... 264/166
5,217,754 A 6/1993 Santiago-Aviles et al.
5,473,008 A * 12/1995 Hessel et al. .............. 524/561
5,707,715 A * 1/1998 de Rochemont
5,762,737 A 6/1998 Bloink et al.

FOREIGN PATENT DOCUMENTS

DE 0 440 570 1/1991
DE 43 16 924 11/1994
EP 1026502 8/2000
GB 492577 9/1938

OTHER PUBLICATIONS

Search Report Dated Mar. 14, 2002.

* cited by examiner

*Primary Examiner*—James Derrington
(74) *Attorney, Agent, or Firm*—Vincent A. Cichosz

(57) ABSTRACT

A method of manufacturing a ceramic body and a gas sensor is disclosed. The method comprises mixing a ceramic material and an organometallic material with a solvent to form a mixture. The organometallic material comprises both a metallic component and an organic ligand. The mixture is disposed onto a surface, dried, and removed to form the ceramic body. The sensor is made by disposing the ceramic body adjacent to an unfired electrolyte body having an electrode disposed on each side thereof to form a green sensor. The green sensor is co-fired to form the sensor.

17 Claims, 2 Drawing Sheets

STEP 1 — MIX AND MILL CERAMIC POWDER, SINTERING AID, SOLVENT AND DISPERSANT TO FORM SLURRY
↓
STEP 2 — ADD ORGANOMETALIC AND MILL A SECOND TIME
↓
STEP 3 — ADD BINDER AND PLASTICIZER, AND MILL A THIRD TIME
↓
STEP 4 — DE-AIR SLURRY
↓
STEP 5 — TAPE-CAST SLURRY
↓
STEP 6 — DRY AND STRIP TO FORM CERAMIC BODY

EXHAUST GAS SENSOR AND THE METHOD OF MANUFACTURE THEREOF

TECHNICAL FIELD

The present disclosure relates generally to gas sensors capable of detecting and measuring exhaust gas compositions. More particularly, the present disclosure relates to ceramic bodies used therein.

BACKGROUND

The automotive industry has used planar exhaust sensors in automotive vehicles for many years to sense the composition of exhaust gases, e.g., oxygen. For example, sensors are used to determine the exhaust gas content for alteration and optimization of the air to fuel ratio for combustion.

A planar exhaust gas sensor typically comprises an electrochemical cell made by the so-called "green tape" lamination method. This method involves building up the electrochemical cell by layering several tapes of green ceramic material along with electrodes and heaters, which are then stacked together in an appropriate design and joined by thermocompression. The resulting elements are then fired to remove the organics in the green tape and to densify the materials into a monolithic unit.

Zirconia and alumina green ceramic tapes can be used to create planar exhaust gas sensors. During oxygen sensor formation, it is necessary to control the relative firing shrinkages of both the alumina and zirconia tapes. In particular, to produce defect free components, it is necessary that the alumina and zirconia tapes have similar end point firing shrinkages. Currently, a number of methods are used to match the firing shrinkage of ceramic tapes such as altering the contents of organics used in tape formulation, altering the ratios of the organic constituents used in tape formulation, varying the type and or molecular weight of the binder and plasticizer used in tape formulation, using finer, more reactive oxide components, and varying thermocompression parameters on the green tape.

While these techniques are commonly used, they do not insure the ability to match firing shrinkages of different tapes. They also can have drawbacks such as increased cost of the tape, higher probability of defects in the tape, increased casting difficulties, and more difficult processing.

SUMMARY

The deficiencies of the above-discussed prior art are overcome or alleviated by a method of manufacturing a ceramic body and a gas sensor. The method of manufacturing the ceramic body comprising: mixing a ceramic material and an organometallic material with a solvent to form a mixture, wherein the organometallic material comprises a metallic component, and an organic ligand; disposing the mixture onto a surface; drying the mixture; and removing the mixture from the surface to form a ceramic body.
The method of making the sensor further comprising: disposing two electrodes on opposite sides of an electrolyte body such that the electrodes are in ionic communication; connecting an electrical lead to each electrode; disposing the ceramic body adjacent to the electrolyte; and co-firing to form a sensor.

BRIEF DESCRIPTION OF THE DRAWINGS

Referring now to the figures, which are meant to be exemplary, and not limiting.

DETAILED DESCRIPTION OF THE PREFERRED EMBODIMENTS

The device and method of manufacture described herein relate to gas sensors. While the particular formulations disclosed herein are related to the production of an oxygen sensor, it should be understood that the device and method described herein are applicable to gas sensors generally.

Figure 1:
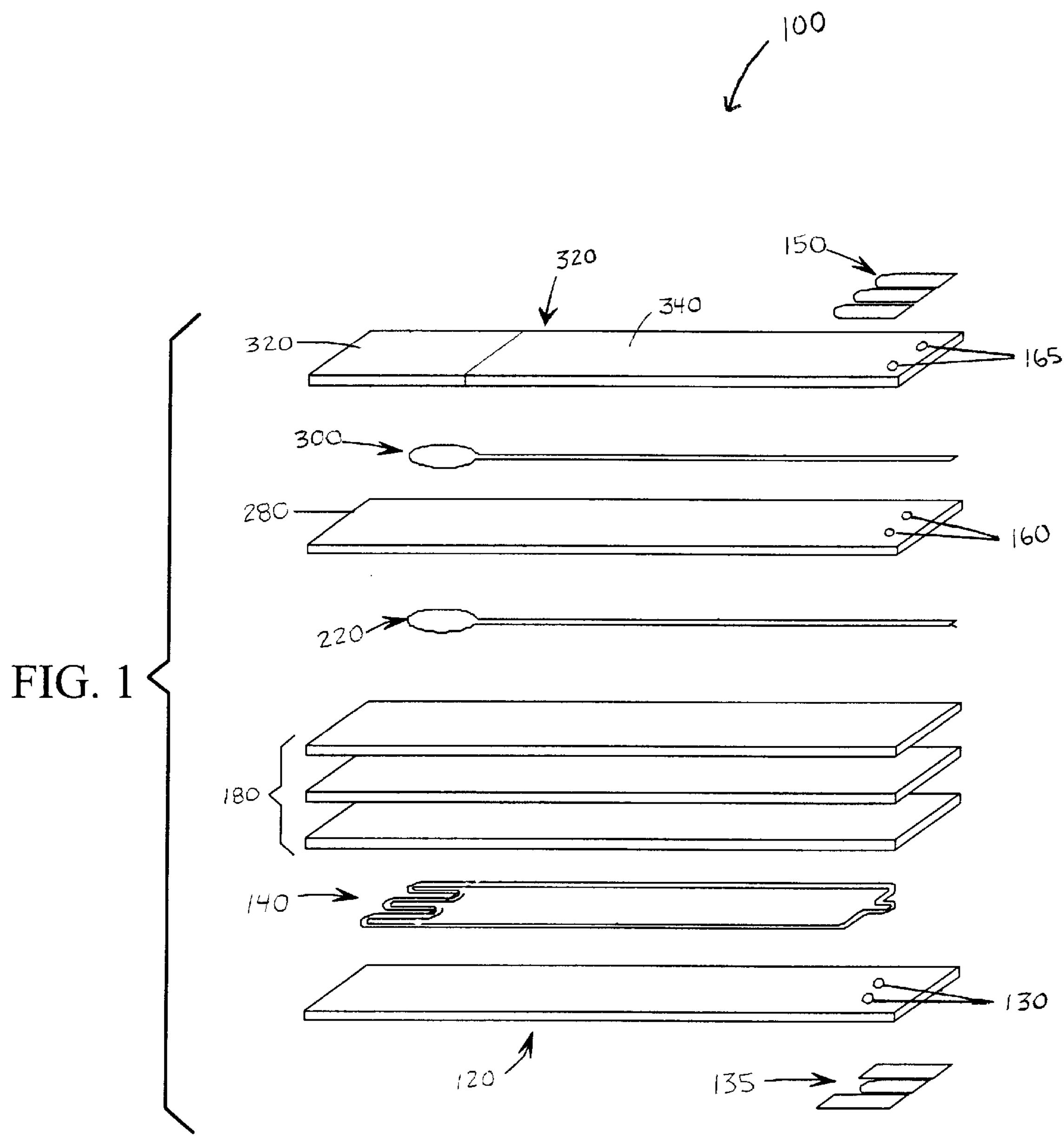
FIG. 1 is a layout of a planar oxygen sensor.

Referring to FIG. 1, an example exhaust gas sensor 100 is shown. For this arrangement, the sensor comprises a ceramic body or substrate 180 disposed adjacent to an electrolyte body portion 280. The electrolyte body portion 280, typically comprises a solid electrolyte, such as yttria doped zirconia or the like. An inner electrode 220 is printed on one side of the electrolyte 280; and an outer electrode 300 is printed on the opposite side of the electrolyte 280. In operation, the inner electrode 220 is exposed to the reference gas such as air. The outer electrode 300 is exposed to a sensing atmosphere such as exhaust gas. The electromotive force (emf) measured between the two electrodes, due to the galvanic potential, which represents the partial pressure difference between the sensing atmosphere and the reference gas, can be used to determine the concentration of oxygen in the exhaust gas.

The sensor 100 further comprises a dielectric alumina tape 120 comprising via holes 130 to provide contact between heater pads 135 and printed heater 140. Typically, one or more heaters are attached to the device to keep the device at a sufficient temperature for sensing operation. The sensor 100 further comprises a protective outer tape 320 which covers the electrolyte 280. The protective outer tape 320 includes a dense ceramic portion 340 and a porous ceramic portion 360. The electrolyte 280 has via holes 160 formed therein, which align with via holes 165 formed in protective outer tape 320, so as to provide electrical communication between pads 150 and inner electrode 220. The electrodes, contact pads, and heater can comprise materials conventionally employed in the sensors, such as platinum, palladium, rhodium, osmium, iridium, ruthenium, and other metals, metal oxides, and other materials, as well as alloys and mixtures comprising at least one of the foregoing materials. Furthermore, other conventional components may be employed such as a lead gettering layer, ground plane, leads, contacts, and the like.

A formulation for producing ceramic bodies (e.g., alumina bodies) comprises at least one ceramic material and at least one organometallic material. Suitable ceramic materials include, but are not limited to, alumina, zirconia, and similar materials, and mixtures comprising at least one of the foregoing ceramic materials. Meanwhile, suitable organometallic materials comprise one or more metallic species with one or more organic ligands bonded thereto. Suitable organometallic materials preferably further comprise a hydroxyl group (OH). A broad range of organometallic materials may be used, as long as the species do not detract from the desired properties of the ceramic tape, such as bulk resistivity, porosity, and stability during the high temperature firing process (e.g., 1,375° C.–1,550° C.) and in the operating environment of an exhaust gas sensor (e.g. up to about 1,000° C.). Preferably, the metal species are selected from Group III metals (i.e., boron, aluminum, gallium, indium, and thallium, as well as mixtures comprising at least one of the foregoing metals), with aluminum (Al) being preferred. A broad range of organic ligands may also be used as long as such ligands do not detract from the desired properties of the ceramic body. Suitable organic ligands are carboxylates, wherein the carboxylate anion ($COO^-$) is bonded to the metallic species. A suitable organometallic material, wherein the metallic species is Al, may have the general structure:

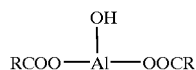

which may also be represented as $(RCOO)_2AlOH$, wherein R is any branched or straight carbon chain suitable to form a carboxylate ligand which does not detract from the desired properties of the ceramic tape (e.g., bulk resistivity, porosity, etc.). Optionally, each R may represent the same or different carboxylates. Suitable carboxylates may be liquid or solid. Preferred carboxylates include hexanoates, neodecanoates, versatates, naphthenates, sterates, benzoates, octoates, phthalates, tallates, and mixtures comprising at least one of the foregoing carboxylates. Some especially preferred carboxylates are 2-ethylhexanoate ($CH_3CH_2CH_2CH_2CH(CH_2CH_3)COO^-$) and cyclohexanebutyrate ($C_6H_{11}CH_2CH_2CH_2COO^-$).

It should be noted that the organometallic material may comprise different types of organic ligands bonded to the same metallic component. For example, the organometallic material may comprise Al as a metallic component and a capric carboxylate ($CH_3(CH_2)_8COO$) as a first ligand and a butyric carboxylate ($CH_3CH_2CH_2COO$) as a second ligand, resulting in an organometallic material having the following structure:

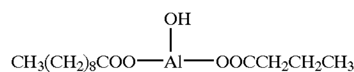

An organometallic material comprising a Group III metal, a hydroxyl group, and two carboxylate ligands, such as, for example, aluminum cyclohexane-butyrate ($(C_6H_{11}CH_2CH_2CH_2COO)_2AlOH$), may bond directly to the ceramic material in a ceramic body. Not to be limited by theory, it is believed that the O—H bond of the hydroxyl group cleaves, allowing the organometallic material to bond directly to the ceramic material.

The amount of organometallic in the ceramic body formulation may be adjusted to manipulate the endpoint shrinkage value of the body. Preferably, the formulation comprises up to about 50 weight percent (wt %), organometallic material, with about 0.5 wt % to about 30 wt % being more preferred, and about 1 wt % to about 15 wt % especially preferred, based upon the total weight of the ceramic slurry (e.g., about 2 wt % to 30 wt % of the dried pre-fired ceramic tape cast (i.e., the solvents have evaporated off leaving alumina powder, organometallics, binders, plasticizer and dispersants)).

Meanwhile, the formulation may comprise about 10 wt % to about 90 wt % ceramic material, with about 25 wt % to about 75 wt % ceramic material preferred, about 30 wt % to about 60 wt % more preferred, and about 40 wt % to about 55 wt % especially preferred. For example, the slurry formulation can have about 3 wt % aluminum organometallic, about 48 wt % aluminum oxide, about 2 wt % glass frit, about 37 wt % solvents, about 6 wt % binders, about 3 wt % plasticizer, and about 1 wt/o dispersants. This results in a dried tape cast having about 5 wt % aluminum organometallic, about 77 wt % aluminum oxide, about 4 wt % glass frit, about 9 wt % binders, about 5 wt % plasticizer, and about 1 wt % dispersant. Once fired, the ceramic is essentially about 100 wt % ceramic with basically no organometallics, binders, plasticizer and dispersants. The fired ceramic has about 94 wt % alumina from alumina powders, about 5 wt % glass frit and about 1 wt % alumina from aluminum organometallic.

In addition to the aforementioned organometallic components and ceramic components, the formulation may further comprise additional materials useful for the formation of a ceramic body, such as solvents, dispersants, sintering aide (s), and/or plasticizer(s). Suitable solvent(s) which include, but are not limited to, organic solvents such as ethanol, xylenes, methanol, similar materials, and water, as well as mixtures comprising at least one of the foregoing, may be present in solvent(s) in an amount of about 5 wt % to about 50 wt %, with about 15 wt % to about 45 wt % preferred, and about 30 wt % to about 40 wt % more preferred, based upon the total weight of the ceramic body before firing.

Also optionally employed are plasticizer(s) in an amount of about 0.01 wt % to about 40 wt %, with about 1 wt % to about 20 wt % preferred, and about 2 wt % to about 8 wt % more preferred, based upon the total weight of the formulation. Suitable plasticizer(s), such as benzyl butyl phthalate, glycols, phthalates, and the like, will preferably impart a desired degree of flexibility to the ceramic components.

In order to promote and stabilize the formulation, dispersant(s), in an amount of about 0.1 wt % to about 20 wt %, with about 0.2 wt % to about 5 wt % preferred, and about 0.2 wt % to about 3 wt % more preferred, and about 0.4 wt % to about 2 wt % especially preferred, based upon the total weight of the formulation, may be employed. Suitable dispersant(s), such as, phosphate ester, Menhaden fish oil, sulfosuccinate, castor oil, and the like, as well as mixtures comprising at least one of the foregoing dispersants, are preferably capable of promoting and stabilizing a dispersion comprising the components described herein.

In addition to the above additives, binder(s) may also be optionally employed in an amount about 1 wt % to about 30 wt %, with about 2 wt % to about 20 wt % preferred, and about 5 wt % to about 10 wt % binder especially preferred, based upon the total weight of the formulation. Suitable binder materials, such as such as polyvinyl butyral, polymethyl methacrylate, polyvinyl formol, and the like, as well as combinations comprising at least one of the foregoing binders, will preferably promote cohesion among the dispersed components. Persons of skill in the art will appreciate that other types of binders will be useful with other types of solvent systems.

As with the binder(s), sintering aide(s) in an amount of about 0.5 wt % to about 25 wt %, with about 0.5 wt % to about 10 wt % preferred, about 0.5 wt % to about 7 wt % more preferred, and about 0.5 wt % and 5 wt % especially preferred. Suitable sintering aides, such as a frit, will preferably help form a glassy phase upon heating.

The percent shrinkage can be determined by measuring the green tape and the fired tape and comparing the results. For example, 475.8 grams aluminum oxide powder and 24.2 grams glass frit powder were weighed and put into a mill. Then, 110 grams of xylene and 110 grams of ethanol and 7.0 grams of Menhaden fish oil, a dispersant and release agent, were added to the mill. The mixture was ball milled for 12 hours in a high purity aluminum oxide lined ball mill with high density, high purity aluminum oxide ⅛ inch diameter mill balls. Then, 74 grams ethanol, 74 grams xylene, 29.2 grams aluminum organometallic, 53.1 grams polyvinyl butyral resin (e.g., Butvar® B-98 Polyvinyl Butyral Resin, commercially available from Solutia Inc., St. Louis, Mo.) and 33.0 grams benzyl butyl phthalate (e.g., Santicizer® 160 Plasticizer, commercially available from Solutia, Inc., St. Louis, Mo.) were added to the mill. The mixture was milled 4 additional hours with binders. The slip was recovered and vacuum de-aired at about 25 mm Hg for 1–3 minutes. The milled mixture was tape cast on non-silicone coated Mylar® film (commercially available from DuPont, Wilmington, Del.) using a doctor blade. The film became a flexible polymer tape, which was removed from the Mylar®. A single tape layer was cut into a several pieces. The pieces were fired to 1,510° C. for 2 hours. The fully fired pieces were re-measured. The shrinkage was determined from the difference between the length of the green part (un-fired) and the length of the same part after firing.

Figure 2:
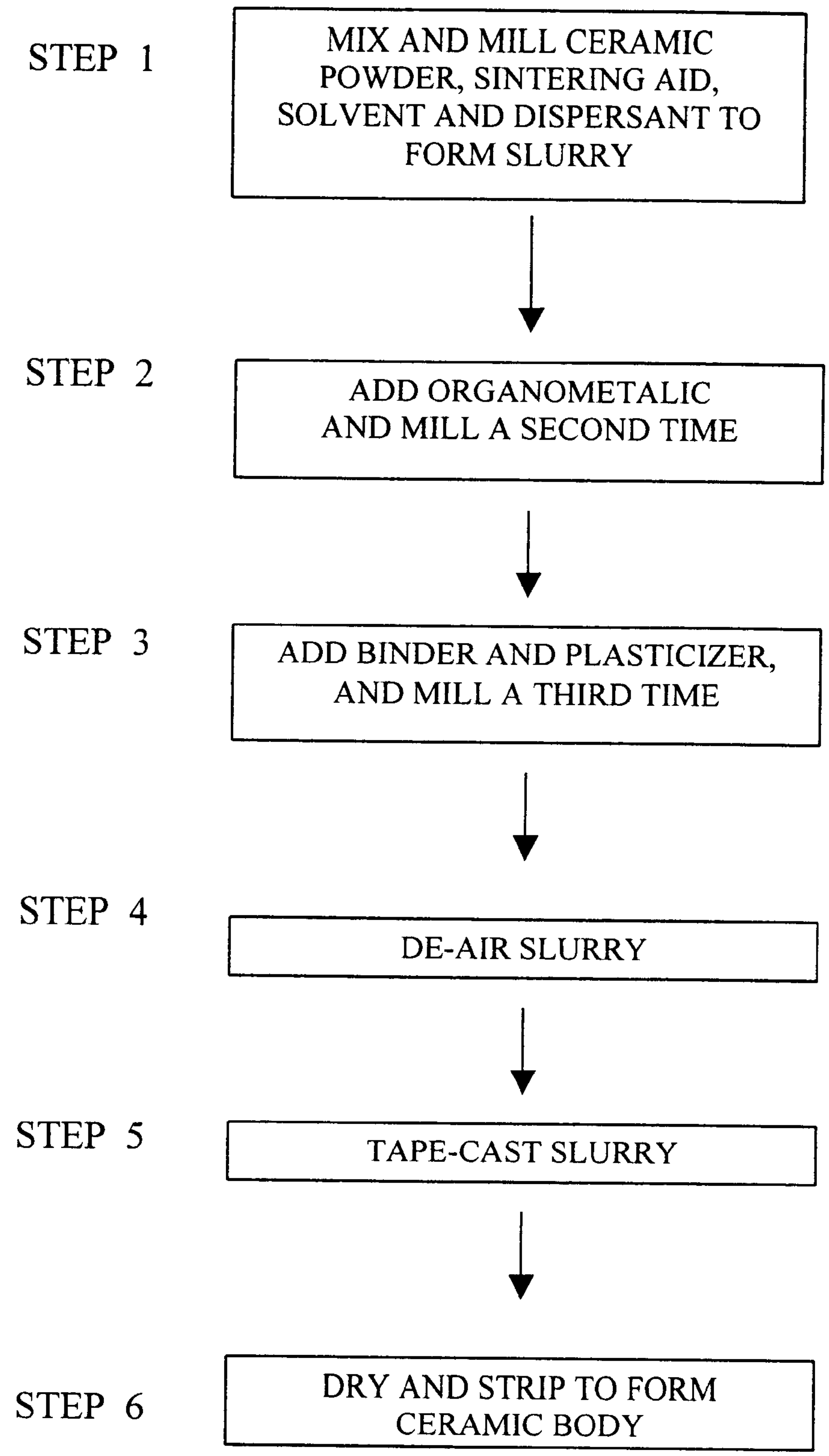
FIG. 2 is a flow chart detailing the method of manufacturing a ceramic body.

FIG. 2 shows an exemplary preparation method for a ceramic body. At STEP 1, ceramic material (e.g., alumina powder), sintering aid, solvent, dispersant, and optionally, organometallic are combined and mixed for a period of time sufficient to disperse the components into a slurry. At STEP 2, additional organometallic material may be added to the slurry, along with additional solvent, if desired, and the slurry may be further mixed.

Optionally, after the mixing of STEP 2, the slurry may be allowed to age. Aging, preferably for a period of time sufficient to allow reactions between the organometallic material and the other slurry components, may be desirable due to competitive absorption among multiple organic species present in the slurry. The competitive adsorption can detrimentally affect slurry dispersion and stability if not allowed to sufficiently progress. Sufficient aging after addition of the organometallic material, e.g., typically about 2 to 12 hours or so, allows for equilibrium to be reached between the organometallic material and the ceramic material.

At STEP 3, binder, plasticizer and, optionally, additional solvent may be added to the slurry, which may then be further mixed. At STEP 4, the slurry may be de-aired, which is typically achieved by pulling a vacuum on the slurry for up to about 3 minutes or so. After de-airing, the slurry may be cast in standard tape casting procedures, as shown at STEP 5. Preferably, the slurry is cast on uncoated polyester film and allowed to dry. After drying, the dried slurry is typically stripped from the polyester film to form an unfired ceramic body, or tape, as shown at STEP 6.

The resulting unfired ceramic body, or tape, may then be fired or can be laid-up with the various other sensor components, e.g., an electrolyte body, with a first electrode and an electrode lead disposed on one side of the electrolyte body, and a second electrode and an electrode lead disposed on a second side. The lay-up is then co-fired, such as in an air atmosphere kiln at a sufficient temperature to achieve close porosity of the dense ceramics (typically about 1,375° C. to about 1,600° C., with a temperature of about 1,500° C. to about 1,550° C. preferred; with a hold for up to about 2 hours or so). Once fired, the co-fired body is disposed next to the remainder of the desired sensor components (e.g., heater(s), ground plane, etc.).

Alternatively, all components can be assembled prior to firing, and then co-fired in a single process to form an integral sensor. In this embodiment, for example, a protective layer may be disposed adjacent to one electrode while the ceramic body is disposed adjacent to the other electrode. Other layers may also be employed include a lead gettering layer disposed between the protective layer and the electrode, and support layers disposed adjacent to the opposite side of the alumina body. Disposed within the support layers can be a ground plane and heater(s). Furthermore, as is well known, an additional electrode(s) with a lead(s) and a porous electrolyte may be disposed between the protective outer tape and the lead gettering layer. Necessary leads, contacts, and vias are also formed on the appropriate layers to connect the electrodes, ground plane and heater(s) accordingly, as is well known in the art.

Persons of skill in the art will recognize that variations in the process are possible without changing the nature of the ceramic tape and/or the sensor. Examples include, but are not limited to, variations of mixing methods and mixing times, variations in the order of component addition, variations of de-airing methods, variations in the amount and frequency of solvent added to the slurry, and variations in firing temperature and time. Furthermore, other sensor configurations may be employed as are conventionally known.

Examples of the formulation for the ceramic body is shown in Table I, wherein tapes A and C were prepared with an organometallic material (aluminum 2-ethylhexanoate). Beside the inclusion of the organometallic material, the formulations and preparation conditions of the Tapes were the same. The formulations of tapes A and C disclose preferred embodiments, while the formulation of tape B represents a standard sensor formulation.

TABLE I

| COMPONENT (grams) | TAPE A | TAPE B | TAPE C |
|---|---|---|---|
| Aluminum 2-ethylhexanoate (organometallic liquid) | 29.2 | 0 | 58.4 |
| Benzyl Butyl Phthalate (Plasticizer) | 33 | 33 | 33 |
| Alumina Powder | 475.83 | 475.83 | 475.83 |
| Frit (Sintering Aid) | 24.17 | 24.17 | 24.17 |
| Ethanol (1) (Solvent) | 110 | 110 | 110 |
| Xylene (1) (Solvent) | 110 | 110 | 110 |
| Menhaden Fish Oil (Dispersant) | 7.0 | 7.0 | 7.0 |
| Ethanol (2) (Solvent) | 74 | 74 | 74 |
| Xylene (2) (Solvent) | 74 | 74 | 74 |
| Polyvinyl Butyral (Binder) | 53.1 | 53.1 | 53.1 |

The ceramic body formed from the above formulations may be laminated to an electrolyte body, e.g., zirconia tape, and fired at a sufficient temperature (e.g., 1,375° C.–1,600° C. for approximately 2 hours) to form a monolithic gas sensor. However, as is understood by persons skilled in the art, the relative firing shrinkages of the ceramic body and the electrolyte body must be closely matched in order to produce a monolithic element, which will function properly as a sensor. Basically, a difference in firing shrinkage of about 0.5% or greater has been found to cause the element to crack. Consequently, a difference in firing shrinkage of about 0.45% or less is preferred, with less than about 0.30% more preferred, less 0.20% or less even more preferred, and about 0.15% or less especially preferred.

Table II shows comparisons of volume percent (vol. %) inorganic material, vol. % organic material, green density (g/cc), and percent of shrinkage during firing (linear in the X and Y directions) (% firing shrinkage) for the above formulations.

TABLE II

| PROPERTY | TAPE A | TAPE B | TAPE C* |
|---|---|---|---|
| Vol. % Inorganic | 53.9 | 53.99 | — |
| Vol. % Organic | 46.1 | 46.01 | — |
| Green Density (g/cc) | 2.457 | 2.696 | — |
| % Firing Shrinkage | 18.13 | 17.51 | 18.3 |

*vol. % inorganic, vol. % organic, and green density were not measured for Tape C.

As can be seen from comparing Table II, the firing shrinkage of the alumina bodies with the organometallic are closest to the firing shrinkage of the zirconia bodies, i.e., within about 0.3%, and preferably within about 0.15%. The ability to manipulate the firing shrinkage enables the employment of higher purity alumina without forming cracks in the fired bodies.

Conventionally, firing shrinkage manipulation is difficult and costly. Manipulation typically involves one or a combination of the following steps: (1) altering the contents of organics used in tape formulation; (2) altering the ratios of the organic constituents used in tape formulation; (3) varying the type and or molecular weight of the binder and plasticizer used in tape formulation; (4) using finer, more reactive oxide components; and (5) varying thermo-compression parameters on the unfired tape. While these techniques are commonly used, they do not insure the ability to match firing shrinkages of different tapes. They also typically lead to increased costs, a higher probability of defects in the tape, increased casting difficulties, and other processing difficulties understood by persons skilled in the art.

The use of the organometallic allows the firing shrinkage of the ceramic body to be easily manipulated by adjusting the amount of organometallic material added to the slurry (e.g., as the amount of organometallic increases, the firing shrinkage increases). Essentially, it is believed that the organometallic (e.g., aluminum 2 ethyl-hexanoate) decomposes on the surface of the alumina particles, which remain in contact with each other. When calcined, the decomposed organometallic creates a very reactive aluminum oxide coating. The high reactivity aluminum oxide coating increases the reactivity between the alumina particles. That increased reactivity increases the shrinkage. In contrast, when organics are burned off, voids are left. As a result, all of the alumina particles are not in contact with each other, and therefore do not all sinter together. This causes the firing shrinkage to be limited.

Moreover, the amount of organometallic material necessary to adjust the firing shrinkage is relatively low in comparison to the other components of the formulation, making other adjustments to the formulation unnecessary. Also, organometallic material is typically low-cost and easily procured.

While preferred embodiments have been shown and described, various modifications and substitutions may be made thereto without departing from the spirit and scope of the invention. Accordingly, it is to be understood that the present invention has been described by way of illustration only, and such illustrations and embodiments as have been disclosed herein are not to be construed as limiting to the claims.

What is claimed is:

1. A method of manufacturing a sensor, comprising:

mixing a ceramic material and an organometallic material with a solvent to form a mixture, wherein the organometallic material comprises a metallic component and an organic ligand;

disposing the mixture onto a surface;

drying the mixture;

removing the mixture from the surface to form a ceramic body;

disposing two electrodes on opposite sides of an electrolyte body such that the electrodes are in ionic communication;

connecting an electrical lead to each electrode;

disposing the ceramic body adjacent to the electrolyte; and co-firing to form the sensor whereby the organometallic material provides enhanced matching of the firing shrinkages of the ceramic and electrolyte bodies.

2. The method of manufacturing the sensor of claim 1, further comprising disposing a protective layer adjacent to the electrolyte body on a side opposite the ceramic body.

3. The method of manufacturing the sensor of claim 1, further comprising disposing support layers adjacent to the ceramic body, with a heater disposed within the support layers.

4. The method of manufacturing the sensor of claim 3, further comprising disposing a ground plane in the support layers, between the heater and the ceramic body.

5. The method of manufacturing the sensor of claim 1, further comprising mixing a dispersant into the mixture.

6. The method of manufacturing the sensor of claim 1, further comprising adding a binder and a plasticizer to the mixture.

7. A method of manufacturing a sensor: comprising:

mixing a ceramic material and an organometallic material with a solvent to form a mixture, wherein the organometallic material comprises a metallic component and an organic ligand;

disposing the mixture onto a surface;

drying the mixture;

removing the mixture from the surface to form a ceramic body;

disposing two electrodes on opposite sides of an electrolyte body such that the electrodes are in ionic communication;

connecting an electrical lead to each electrode;

disposing the ceramic body adjacent to the electrolyte; and co-firing to form the sensor;

wherein the ceramic body has a ceramic body firing shrinkage and the electrolyte body has an electrolyte body firing shrinkage, and wherein a firing shrinkage difference between the ceramic body firing shrinkage and the electrolyte body firing shrinkage is about 0.45% or less.

8. The method of manufacturing the sensor of claim 7, wherein the firing shrinkage difference is about 0.30% or less.

9. The method of manufacturing the sensor of claim 8, wherein the firing shrinkage difference is about 0.20% or less.

10. The method of manufacturing the sensor of claim 8, wherein the firing shrinkage difference is about 0.15% or less.

11. The method of manufacturing the sensor of claim 1, further comprising de-airing the mixture.

12. The method of manufacturing the sensor of claim 1, wherein the ceramic material is selected from the group consisting of alumina, zirconia, and mixtures comprising at least one of the foregoing ceramic materials.

13. The method of manufacturing the sensor of claim 1, wherein the metallic component is selected from the group consisting of boron, aluminum, gallium, indium, thallium and mixtures comprising at least one of the foregoing metallic components.

14. The method of manufacturing the sensor of claim 13, wherein the metallic component is aluminum.

15. The method of manufacturing the sensor of claim 1, wherein the organic ligand comprises a first carboxylate group and a second carboxylate group, the first and second carboxylate groups comprising branched or straight carbon chains.

16. The method of manufacturing the sensor of claim 15, wherein the organic ligand is selected from the group consisting of hexanoates, neodecanoates, versatates, naphthenates, sterates, benzoates, octoates, phthalates, tallates, and mixtures comprising at least one of the foregoing organic ligands.

17. The method of manufacturing the sensor of claim 1 wherein the electrolyte body comprises zirconia.

* * * * *